United States Patent
Hall et al.

(10) Patent No.: US 10,722,120 B1
(45) Date of Patent: Jul. 28, 2020

(54) SENSOR PLATFORM ARRAY THAT MOVES SENSOR PLATFORMS TO CONFORM TO THE SHAPE OF THE SUBJECT TO BE MONITORED

(71) Applicants: David R. Hall, Provo, UT (US); Joshua Larsen, Spanish Fork, UT (US); Jared Reynolds, Pleasant Grove, UT (US); Daniel Hendricks, Provo, UT (US); Travis Niederhauser, Mapleton, UT (US); K. Jeffrey Campbell, Spanish Fork, UT (US); Steven J. M. Butala, Provo, UT (US); Vivek Garg, Murray, UT (US)

(72) Inventors: David R. Hall, Provo, UT (US); Joshua Larsen, Spanish Fork, UT (US); Jared Reynolds, Pleasant Grove, UT (US); Daniel Hendricks, Provo, UT (US); Travis Niederhauser, Mapleton, UT (US); K. Jeffrey Campbell, Spanish Fork, UT (US); Steven J. M. Butala, Provo, UT (US); Vivek Garg, Murray, UT (US)

(73) Assignee: Hall Labs LLC, Provo, UT (US)

( * ) Notice: Subject to any disclaimer, the term of this patent is extended or adjusted under 35 U.S.C. 154(b) by 0 days.

(21) Appl. No.: 16/272,206

(22) Filed: Feb. 11, 2019

(51) Int. Cl.
*A61B 5/00* (2006.01)
*A47K 13/24* (2006.01)
*G01L 1/26* (2006.01)

(52) U.S. Cl.
CPC ............ *A61B 5/0053* (2013.01); *A47K 13/24* (2013.01); *A61B 5/0024* (2013.01); *G01L 1/26* (2013.01)

(58) Field of Classification Search
CPC ... A61B 5/0022; A61B 5/0024; A61B 5/0053; A61B 5/01; A61B 5/02055; A61B 2562/0247; G16H 40/63; A47K 13/24; G01L 1/26
See application file for complete search history.

(56) References Cited

U.S. PATENT DOCUMENTS

| | | | |
|---|---|---|---|
| 2014/0163402 A1* | 6/2014 | Lamego | A61B 5/02141 600/493 |
| 2014/0371607 A1* | 12/2014 | Fitzsimmons | A61B 5/0004 600/499 |
| 2016/0270948 A1* | 9/2016 | Hariri | A61H 9/0078 |
| 2016/0379461 A1* | 12/2016 | Gaidar | G08B 21/0453 340/573.1 |
| 2017/0238825 A9* | 8/2017 | Fitzsimons | A61B 5/0004 |
| 2017/0273695 A1* | 9/2017 | Ganske | A61N 1/39 |

(Continued)

*Primary Examiner* — Orlando Bousono

(57) ABSTRACT

The sensor platform array includes a plurality of sensors and one or more sensor platforms. Each sensor may be mounted on a sensor platform. The sensor platform may be mounted on a support panel. The support panel may be mounted on a toilet lid. The one or more sensor platforms may be extendable towards a user seated on the toilet. Each sensor may be independently extended so that it is positioned flush against a user's body. The sensor platform array may include bendable arms which reach around a user and place sensors on the ventral side of the user. The sensors may collect measurements which are relevant to the user's health and well-being. In some embodiments, the sensors may be removable and replaceable so that different sensors may be added according to a user's individual needs.

18 Claims, 7 Drawing Sheets

(56) References Cited

U.S. PATENT DOCUMENTS

| | | | |
|---|---|---|---|
| 2018/0055681 A1* | 3/2018 | Hariri | A61F 5/56 |
| 2018/0333055 A1* | 11/2018 | Lamego | A61B 5/02141 |
| 2019/0104953 A1* | 4/2019 | Narasimhan | A61B 5/02241 |
| 2019/0201268 A1* | 7/2019 | Sayadi | A47C 21/003 |
| 2019/0201269 A1* | 7/2019 | Sayadi | A47C 21/003 |
| 2019/0209405 A1* | 7/2019 | Sayadi | A47C 21/003 |

* cited by examiner

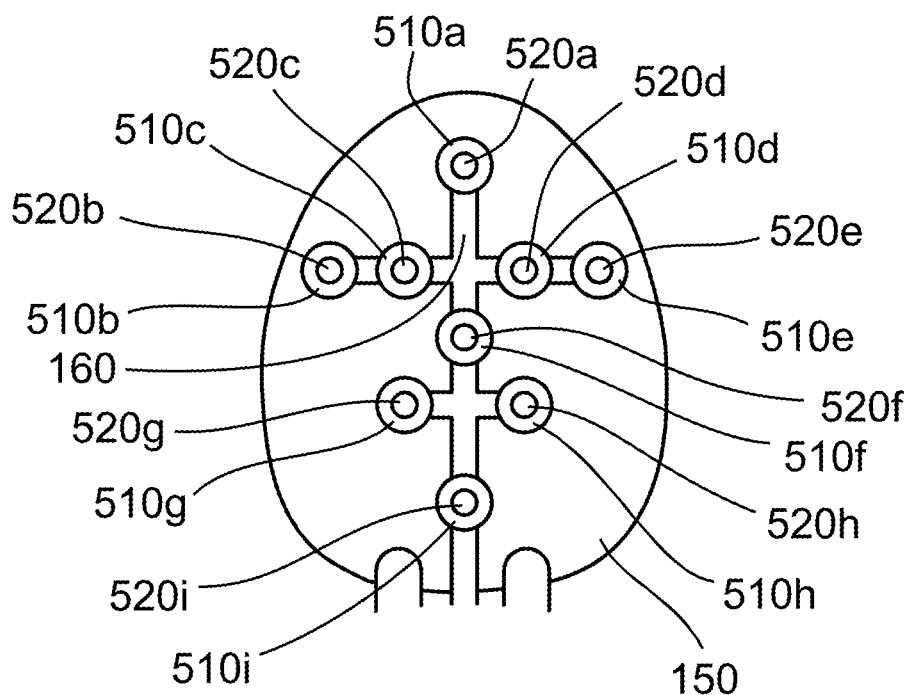
FIG. 5A
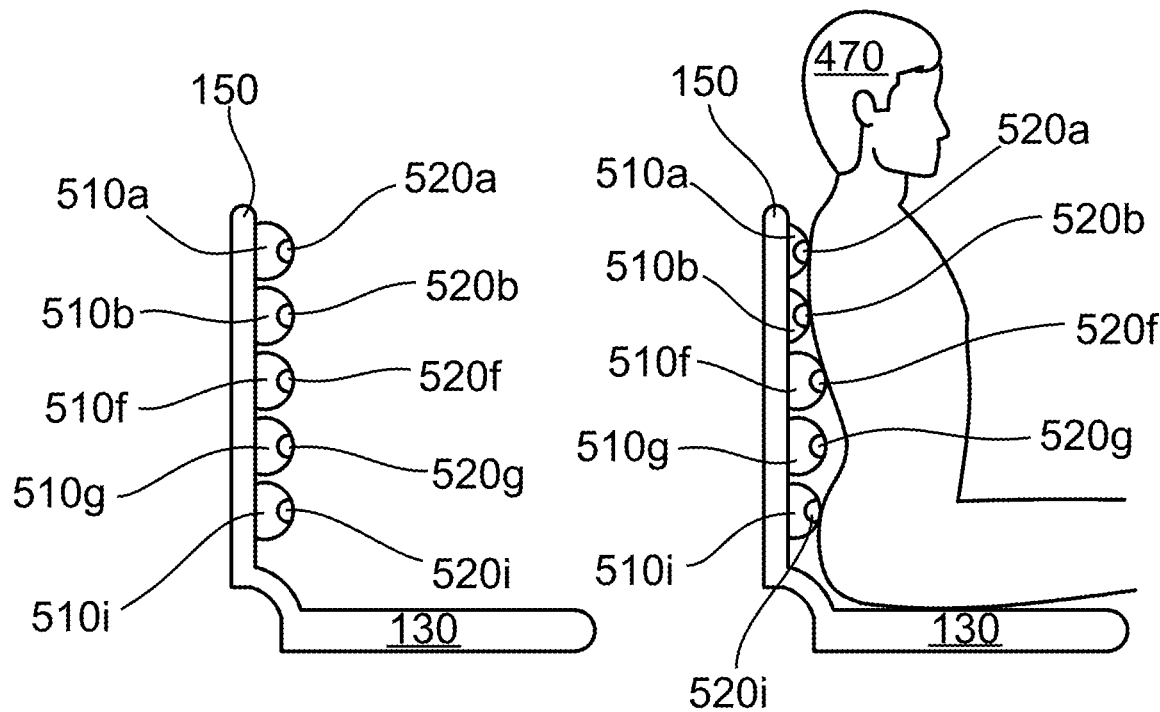
FIG. 5B
FIG. 5C

SENSOR PLATFORM ARRAY THAT MOVES SENSOR PLATFORMS TO CONFORM TO THE SHAPE OF THE SUBJECT TO BE MONITORED

BACKGROUND

Field of the Invention

This disclosure relates to devices which collect measurements that are relative to a user's health status.

Background of the Invention

Nearly everyone uses the toilet multiple times per day. Medical toilets collect measurements related to a user's health status while the user is depositing waste in the medical toilet. The user may use the medical toilet as one would use a traditional toilet except that the medical toilet collects measurements that are relevant to the user's health status. The measurements are collected without significantly impacting the user's daily routine. In addition, measurements may be taken more often with a medical toilet than would occur using other devices. This results in a more complete data set to be used to assess the user's health.

Some medical toilets include sensors in the toilet seat because the toilet seat may come in contact with the bare skin of the legs. However, for purposes of collecting health related measurements, the toilet seat is a significant distance away from the vital organs of the body. More specifically, the distance between sensors in the toilet seat and the vital organs will cause a reduction in the quality of measurements collected from those organs.

Unfortunately, the vital organs, many of which are located in the torso, are often the precise areas that are useful to monitor for purposes of tracking a user's health. Therefore, from a medical sensing perspective, it would be valuable to also have sensors placed on one or more of the back, torso, and neck because those areas are close to the heart, lungs, stomach, throat, and intestines. However, it would be inconvenient, difficult, or even impossible for the toilet user to place sensors on his or her own back, neck, and torso. Furthermore, it would be inconvenient, and defeat the purpose of having automated sensors on a toilet, to require another person to place the sensors on the user. Thus, there is a need for an automated, mechanized system for back, torso, and neck sensor placement.

BRIEF SUMMARY OF THE INVENTION

We disclose a sensor platform array which may be used on a medical toilet. The sensor platform array may be positioned on the medical toilet such that it is behind a user seated on the medical toilet. In other words, the sensor platform array may be positioned on or behind a rear section of the toilet seat on the medical toilet. In some embodiments, the sensor platform array may be positioned on a toilet lid.

The sensor platform array may include sensors which may collect measurements that are relevant to a user's health or well-being. These measurements may be physiological measurements. The sensors may be removable and exchangeable so that the compliment of sensors may be customized to each user. The sensor platform array may include a support structure which is in connection with one or more automated mechanical apparatus which may move the sensors so that they may be brought in physical contact with a user's head, neck, arms, torso, and other body parts.

In some embodiments, the automated mechanical apparatus includes a cylinder-piston assembly which may have a ball joint on the distal end of the piston. A sensor platform may be also be connected to the ball joint. The surface of each sensor platform on the sensor platform array may move to conform to the shape of the user so that physical contact between the sensors and the clothing or skin of the user is optimized. In some embodiments, the piston may be pneumatic or hydraulic.

Alternatively, the automated mechanical apparatus may include one or more inflatable cells with at least one sensor mounted thereon. In these embodiments, the inflatable cell is the sensor platform. A pump directs gas into the one or more inflatable cell to expand it such that it extends toward a user seated on the medical toilet. The surface of each of the one or more inflatable cell on the sensor platform array may mold itself to conform to the shape of the user so that physical contact between the sensors and the clothing or skin of the user is optimized.

The sensor platform array may include a conformational control system which may include one or a plurality of pressure sensors. Each pressure sensor may be in communication with the sensor platform. The conformation control system may further include a controller which is in electronic communication with each pressure sensor. The controller may include non-transitory computer readable medium comprising instructions for actuating a pump associated with the sensor platform array. The pump may direct gas into the inflatable cell causing it to extend toward a user. Eventually, the pressure sensors may detect an increase in pressure when the sensor platform is extended far enough to contact a surface of a user. Upon detecting the increase in pressure, the pressure sensors may send a signal to the controller and the instructions may cause the controller to send a signal to the pump causing it to stop pumping gas into the inflatable cell or pneumatic piston or stop pumping liquid into the hydraulic piston. Consequently, the sensors extend enough to be flush with a surface of a user but no more.

The controller may also include a memory to store signals the controller receives from the sensors. The non-transitory computer readable medium may include instructions for analyzing the signals received by the controller or stored in the memory.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

FIG. 5A illustrates a front view of an embodiment of the disclosed sensor array platform which includes multiple inflatable cells.

FIG. 5B illustrates a side view of the sensor array platform of FIG. 5A.

FIG. 5C illustrates a side view of the sensor array platform of FIG. 5A during use.

DETAILED DESCRIPTION OF THE INVENTION

Definitions

Figure 1A:
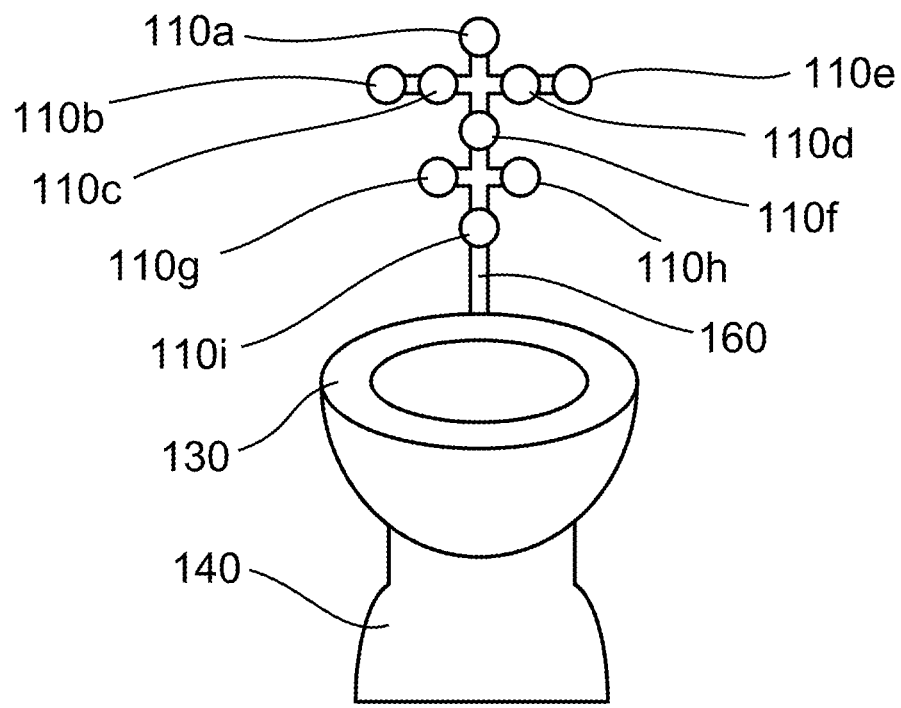
FIG. 1A illustrates an embodiment of the disclosed sensor platform array.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a sensor platform array which may support a plurality of sensors and which may be mounted on a medical toilet, in particular, on the toilet lid. The sensor platform may have automated mechanical apparatuses which may move the sensors so that they may be brought in physical contact with a user's head, neck, arms, torso, and other body parts. The surface of each sensor platform on the sensor platform array may move to conform to the shape of the user so that physical contact between the sensors and the clothing or skin of the user is optimized.

In some embodiments, the sensor platform array includes a support panel and a plurality of sensor-inflatable cell assemblies. The sensor-inflatable cell assemblies may be mounted on the support panel. Each of the sensor-inflatable cell assemblies may include one or more inflatable cells. One or more sensors may be mounted on each of the one or more inflatable cells. The one or more sensors may collect measurements which are relevant to a user's health and well-being. These measurements may include physiological measurements. For example, the sensors may include one or more of the following list: a stethoscope, an ultrasound probe, an echocardiogram probe, a temperature sensor, a durometer, an electrocardiogram lead, and a ballistocardiography sensor. The one or more sensors may include pressure sensors which send a signal to a controller when the sensor detects an increase in pressure. In some embodiments, the sensors and/or the sensor-inflatable cell assemblies may be removable and exchangeable. Accordingly, the sensors may be customized to meet a user's individual needs at any given time.

In some embodiments, the sensor platform array includes a gas pump. The gas pump may be in fluid connection with the at least one inflatable cell to provide gas which inflates the at least one inflatable cell. In embodiments which include a plurality of sensor-inflatable cell assemblies, the gas pump may supply gas to inflate each inflatable cell.

In some embodiments, the sensor platform array may include a conformation control system which may include one or a plurality of pressure sensors. Each pressure sensor may be in communication with the inflatable cell within one of the plurality of sensor-inflatable cell assemblies. The conformation control system may further include a controller which is in electronic communication with each pressure sensor. The controller may include non-transitory computer readable medium comprising instructions for actuating a pump associated with the sensor platform array. The pump may direct gas into the inflatable cells causing them to extend toward a user. Eventually, the pressure sensors may detect an increase in pressure when the inflatable cell is extended far enough to contact a surface of a user. The pressure sensors may send a signal to the controller and the instructions may cause the controller to send a signal to the pump to stop pumping gas into the inflatable cell associated with the pressure sensors which sent the signal.

In some embodiments, the sensor platform array includes a single inflatable cell mounted on a support panel. One or a plurality of sensors may be disposed on the inflatable cell. As with the embodiment described above, the sensors may collect measurements which are relevant to a user's health and well-being. These measurements may include physiological measurements. For example, the sensors may include one or more of the following list: a stethoscope, an ultrasound probe, an echocardiogram probe, a temperature sensor, a durometer, an electrocardiogram lead, and a ballistocardiography sensor. The one or more sensors may include pressure sensors which send a signal to a controller when the sensor detects an increase in pressure. In some embodiments, the sensors may be removable and exchangeable. Accordingly, the sensors may be customized to meet a user's individual needs at any given time. In some embodiments, this sensor platform array may be mounted on a toilet lid.

This embodiment may also include a gas pump. The gas pump may be in fluid connection with the single inflatable cell to provide gas which inflates the single inflatable cell.

This embodiment may also include a conformational control system, similar to that described in the embodiment that comprises multiple sensor-inflatable cell assemblies. The conformation control system which may include one or a plurality of pressure sensors. Each pressure sensor may be in communication with the single inflatable cell. The conformation control system may further include a controller which is in electronic communication with each pressure sensor. The controller may include non-transitory computer readable medium comprising instructions for actuating a pump associated with the sensor platform array. The pump may direct gas into the inflatable cell causing it to extend toward a user. Eventually, the pressure sensors may detect an increase in pressure when the inflatable cell is extended far enough to contact a surface of a user. The pressure sensors may send a signal to the controller and the instructions may cause the controller to send a signal to the pump to stop pumping gas into the inflatable cell.

Some embodiments include a support panel as described elsewhere herein with a plurality of cylinder-piston assemblies in connection with the support panel. The support panel may extend vertically above the toilet bowl and be positioned such that the support panel is behind a user seated on the toilet seat of the medical toilet. Each cylinder-piston assembly may include a piston within a cylinder. The piston may be hydraulic or it may be pneumatic. A ball joint may be positioned on a distal end of the piston relative to the support panel. The ball joint may also be in connection with a sensor platform. The sensor platform may rotate on the ball joint so that the sensor platform may be flush with a surface of a user. One or more sensors may be positioned on the sensor platform.

This embodiment may also include a conformation control system comprising a controller. One or more of the sensors may be a pressure sensor which sends a signal to the controller when the pressure sensor experiences an increase in pressure. This may occur when the sensor platform and sensor contact a surface of a user. The controller may include non-transitory computer readable medium comprising instructions for actuating a device which causes the piston to extend toward the user. For example, in embodiments which include a pneumatic piston, the device may be a gas pump. The gas pump may direct gas to the cylinder-piston assemblies causing them to extend toward a user. In embodiments which include a hydraulic piston, the device may pump liquid into the cylinder-piston assemblies. Eventually, the pressure sensors may detect an increase in pressure when the sensor platform is extended far enough to contact a surface of a user. The pressure sensors may send a signal to the controller and the instructions may cause the controller to send a signal to the device causing it to stop extending the piston. In the example of the pneumatic piston, the instructions cause the gas pump to stop pumping gas into the cylinder-piston assembly associated with the pressure sensor which sent the signal. In the example of the hydraulic piston, the instructions cause the pump to stop pumping liquid into the cylinder-piston assembly associated with the pressure sensor which sent the signal.

Any of the embodiments disclosed herein may include at least one bendable arm which may extend from the support panel. Each bendable arm may include at least one hinge which enables the arm to bend and wrap around a user seated on a toilet on which the sensor platform array is mounted. Each bendable arm may include at least one sensor which may collect measurements which are relevant to a user's health and well-being. These measurements may include physiological measurements. For example, the sensors may include one or more of the following list: a stethoscope, an ultrasound probe, an echocardiogram probe, a temperature sensor, a durometer, an electrocardiogram lead, and a ballistocardiography sensor. Examples of measurements which may be collected from the ventral (front) of a user's body include heart rate, electrocardiogram measurements, ultrasound imaging of vital organs, bowel sounds, heart rate, heart rhythm, breath analysis, and body or skin temperature.

Any of the embodiments disclosed herein, may include a controller which is in electrical communication with the sensor, the one or more sensor-inflatable cell assemblies, or the cylinder-piston arrays. The controller may include a memory on which signals produced by the sensors may be stored for later use. The controller may include non-transitory computer readable media which comprises instructions for creating an analysis of the signals received by the sensors or stored in the memory.

Referring now to the drawings, FIG. 1A illustrates an embodiment of a sensor platform array which is positioned on a medical toilet. The medical toilet includes toilet seat 130 and base 140. In this embodiment, the sensor platform array is positioned behind toilet seat 130 like a toilet lid in the raised (vertical) position although a traditional toilet lid is absent. The sensor platform array includes sensor platforms 110*a*, 110*b*, 110*c*, 110*d*, 110*e*, 110*f*, 110*h*, and 110*i* which may be individually controlled and moved to conform to the surface of the user. Sensor platforms 110*a-i* are mounted on support structure 160 that may include mechanized joints that aid in moving the sensor platforms to the surface of the user. Each of sensor platforms 110*a-i* may include a means for independent movement as disclosed herein. One or more of a plurality of sensors which may collect measurements relevant to a user's health and well-being may be mounted on each of sensor platforms 110*a-i*.

Figure 1B:
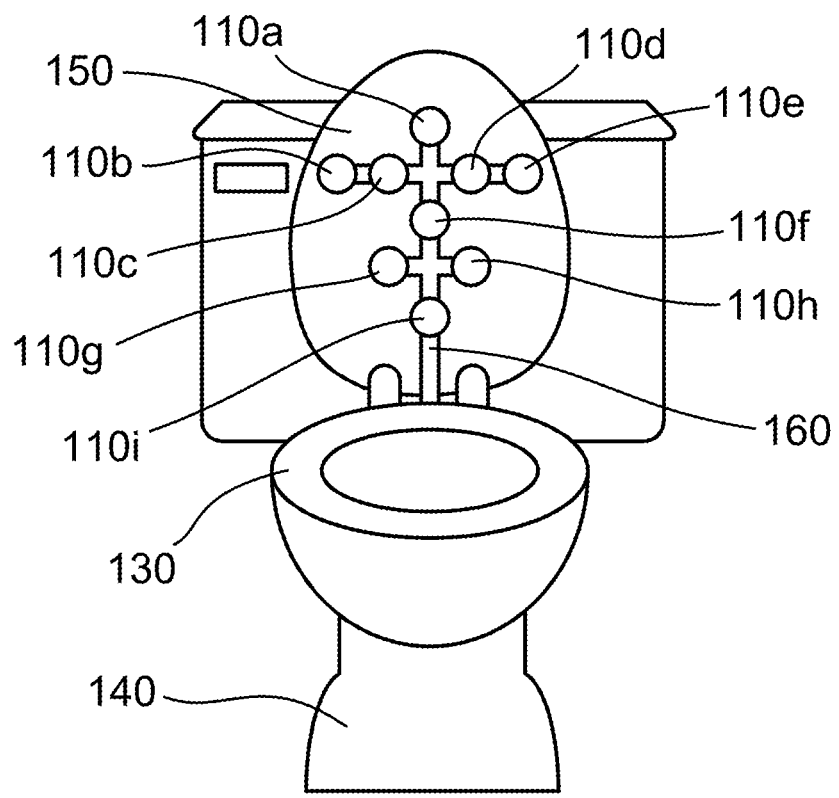
FIG. 1B illustrates an embodiment of the disclosed sensor platform array which is mounted on a toilet lid.

FIG. 1B illustrates the sensor platform array of FIG. 1A on the medical toilet. The embodiment of FIG. 1B includes toilet lid 130 on which the sensor platform array is mounted. In this embodiment, support structure 160 is directly or indirectly in contact with toilet lid 130 to connect the sensor platform array to toilet lid 130.

Figure 2:
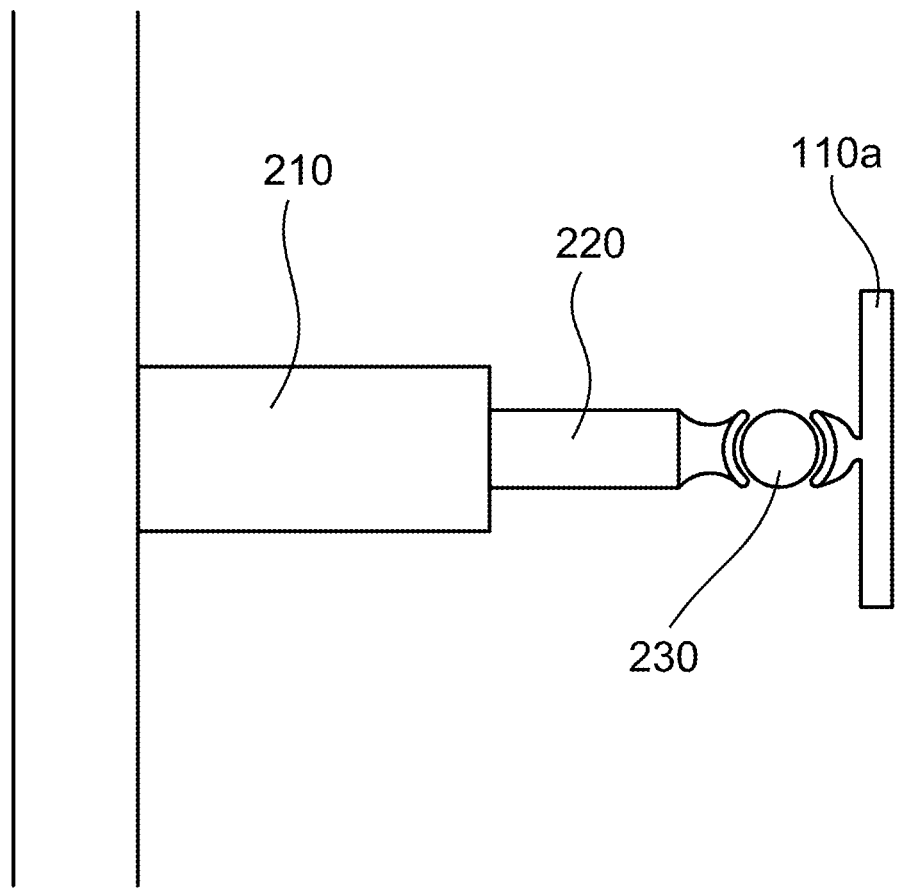
FIG. 2 illustrates an embodiment of a single sensor platform which includes a cylinder-piston assembly.

FIG. 2 illustrates an embodiment of a single sensor platform as illustrated in FIGS. 1A and 1B that may be extended and retracted to move to and from the surface of the user, for example, the user's back. Cylinder 210 is connected to support structure 160 and extends outward from support structure 160 toward a user seated on a toilet seat. Piston 220 is inserted within cylinder 210 forming a cylinder-piston assembly. Piston 220 may move horizontally through cylinder 210 toward and away from a user who is seated on a toilet as shown in FIGS. 1A and 1B. Ball joint 230 is positioned between piston 220 and sensor platform 110*a* and connected to both. Ball joint 230 aids conformance of sensor platform 110*a* to the surface of the user by enabling sensor platform 110*a* to rotate on ball joint 230. This rotation may place sensor platform 110*a* flush with a surface of a user. In some embodiments, the cylinder-piston assembly may be hydraulic and in others it may be pneumatic.

Figures 3A, 3B:
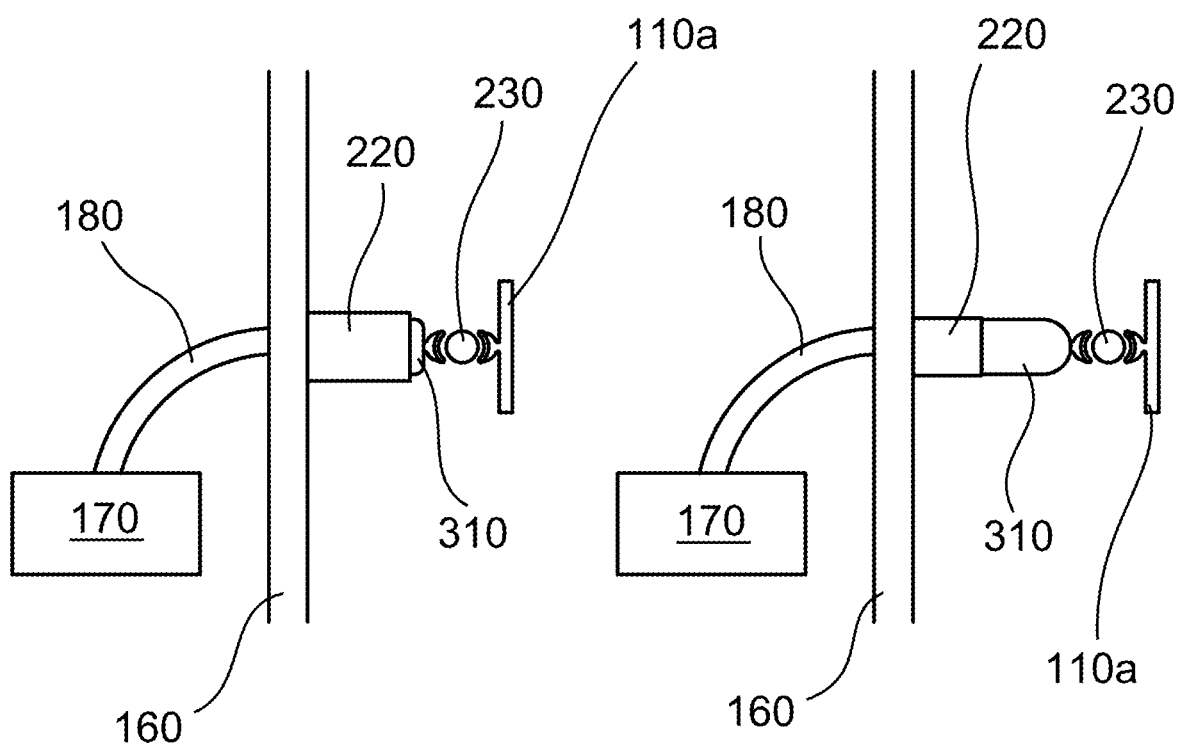
FIGS. 3A and 3B illustrate an embodiment of a single sensor platform which includes an inflatable cell in a deflated (FIG. 3A) and an inflated (FIG. 3B) position.

FIGS. 3A and 3B illustrate an embodiment of a single sensor platform as illustrated in FIG. 1 that may be extended and retracted to move towards and away from the surface of the user. Similar to the embodiment of FIG. 2, cylinder 220 is connected to and extends from support structure 160. Inflatable cell 310 within cylinder 220 is shown deflated in FIG. 3A and inflated in FIG. 3B. Pump 170 moves gas through conduit 180 and into inflatable cell 310 causing inflatable cell 310 to inflate as shown in FIG. 3B. When inflatable cell 310 is deflated as shown in FIG. 3A, it retracts into cylinder 220. As inflatable cell 310 is filled with gas, it extends outward from cylinder 220. Inflatable cell 310 is in connection with ball joint 230 which, in turn, is in connection with sensor platform 110a. Sensor platform 110a extends proportionally as inflatable cell 310 is inflated and moves outward and away from support structure 160. In FIG. 3B, inflatable cell 310 is fully inflated and, consequently, sensor platform 110a is fully extended. Alternatively, inflatable cell 310 may be partially inflated in which case sensor platform 110a may be partially extended. As in the embodiment of FIG. 2, sensor platform 110a may rotate on ball joint 230 which enables sensor platform 110a to conform to rest flush with a surface of a user.

Figure 4A:
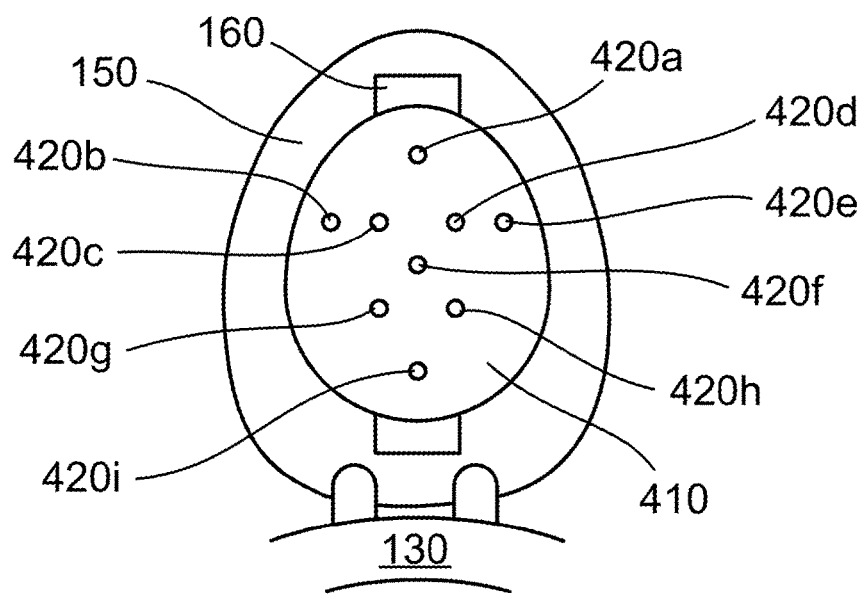
FIG. 4A illustrates a front view of an embodiment of the disclosed sensor array platform including a single inflatable cell.

FIG. 4A illustrates a front view of yet another embodiment of the disclosed sensor platform array. Inflatable cell 410 is mounted on support structure 160. This embodiment includes a single inflatable cell on which are mounted a plurality of sensors (sensors 420a-i). One or more of sensors 420a-i may be a pressure sensor which senses when inflatable cell 410 comes in contact with a surface of a user. When the pressure sensor(s) detect a change in pressure, they may send a signal to a controller which may be in electronic communication with the pressure sensor(s). The controller may then send a signal to a pump, similar to that shown in FIGS. 3A and 3B, which supplies gas to inflatable cell 410. The signal from the controller may deactivate the pump causing it to cease to provide gas to inflatable cell 410.

Figures 4B, 4C:
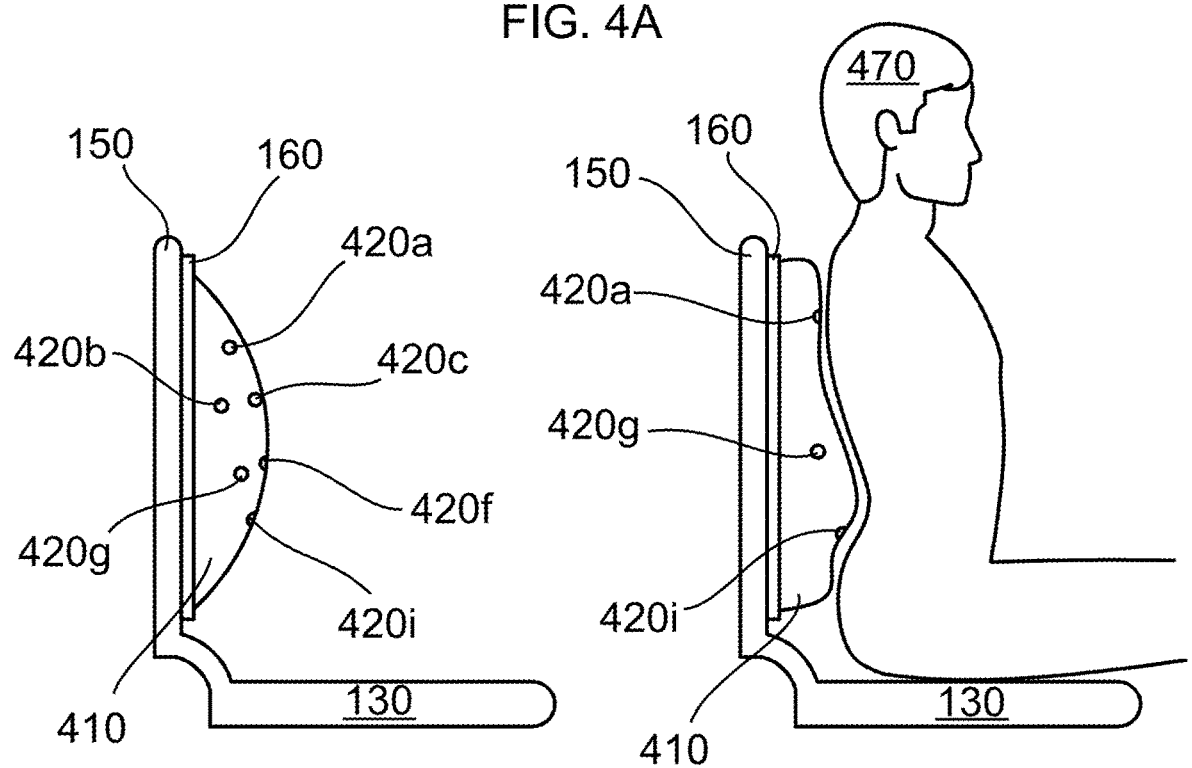
FIG. 4B illustrates a side view of the sensor array platform of FIG. 4A.
FIG. 4C illustrates a side view of the sensor array platform of FIG. 4A during use.

As shown in FIGS. 4A-C, this embodiment is mounted on toilet lid 150 by adhering support structure 160 to toilet lid 150. Toilet lid 150 is mounted on a toilet which includes toilet seat 130.

FIG. 4B shows a side view of the embodiment of FIG. 4A in which inflatable cell 410 is fully inflated. FIG. 4C shows the same view as FIG. 4C except that user 470 is seated on toilet seat 130. Inflatable cell 410 is inflated to the point that it is flush with the back of user 470 all along the user' dorsal torso. Each of sensors 420a-i is also flush with the back of user 470 enabling each sensor to collect a measurement which may be relevant to the health and well-being of user 470.

FIGS. 5A-C illustrate yet another embodiment of the disclosed sensor platform array. FIG. 5A illustrates a front view of an embodiment which includes support structure 160 which is similar to that shown in FIGS. 1A and 1B. Support structure 160 is mounted on toilet lid 150. Inflatable cells 510a-i are mounted on support structure 160. One of sensors 520a-i is mounted on each of inflatable cells 510a-i. Consequently, inflatable cells 510a-i each function as a sensor platform. This embodiment may include a pump and a conduit as shown in FIGS. 3A and 3B and which provides gas to inflate each of inflatable cells 510a-i.

FIG. 5B shows a side view of the embodiment of FIG. 5A. Inflatable cells 510a-i are inflated and thus sensors 520a-i are extended toward the front of the toilet. FIG. 5C shows the same view as FIG. 5B with user 470 seated on toilet seat 130. Inflatable cells 510a-i are inflated to the level necessary to place sensors 520a-i flush with the back of user 470. For example, inflatable cells 510a and 510b are inflated to a lesser extent than inflatable cells 510f and 510g.

Figure 6:
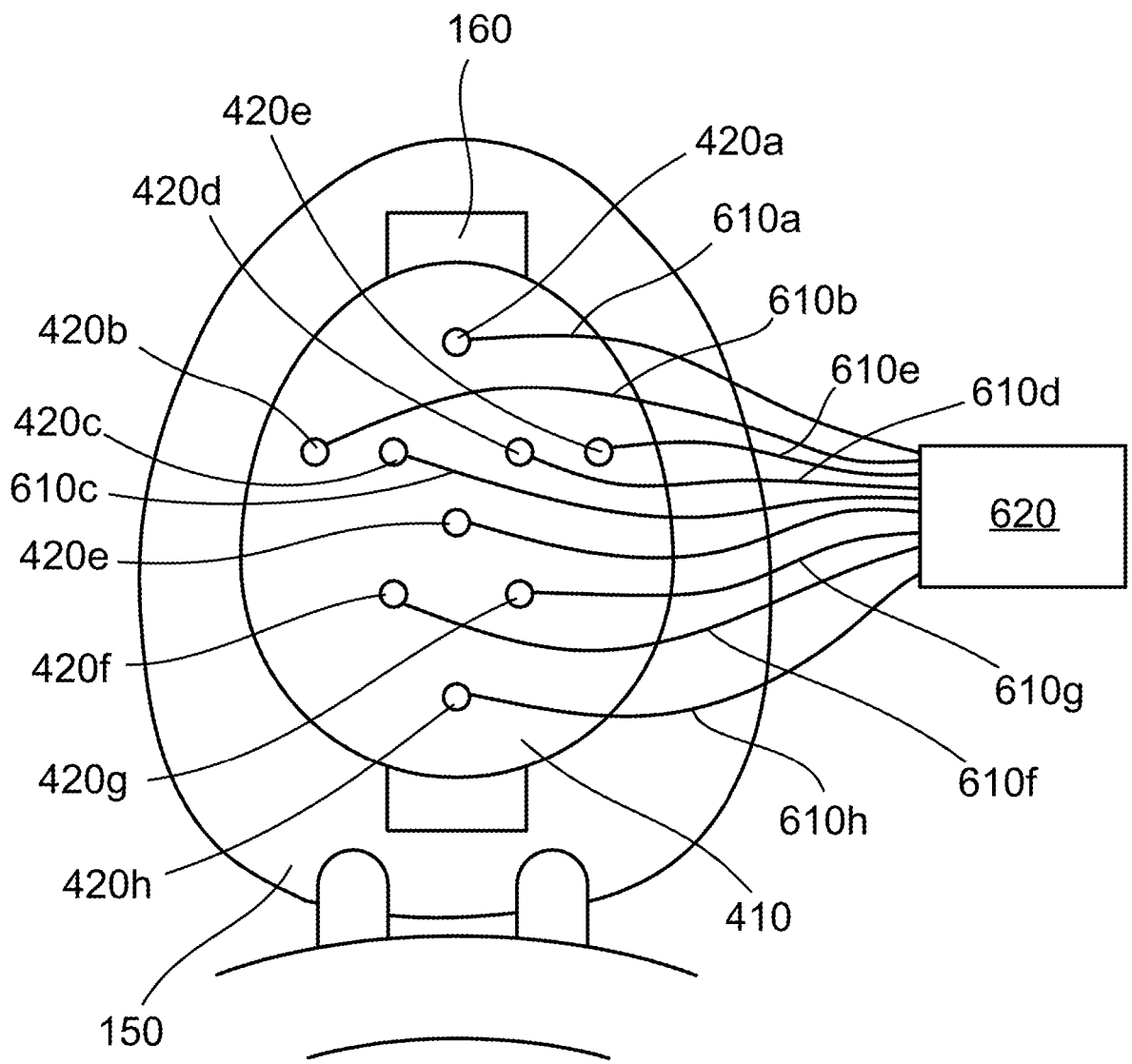
FIG. 6 illustrates an embodiment of the disclosed sensor platform array with the sensors in electronic connection with a controller.

FIG. 6 illustrates the sensor platform array similar to that show in FIG. 4A. Electrical wires 610a-i connect sensors 420a-i to controller 620. More or more of sensors 420a-i may be a pressure sensor. When inflatable cell 410 and, consequently, the one or more pressure sensor, comes in contact with a surface on a user, the rise in pressure may be communicated to controller 620. Non-transitory computer readable medium on controller 20 may interpret the rise in pressure as contact with a user's body. Controller 620 may then signal a pump which provides gas to inflatable cell 410 to stop pumping gas into inflatable cell 410. Inflatable cell 410, which, in this embodiment, functions as the sensor platform, ceases to extend toward the user.

Figure 7A:
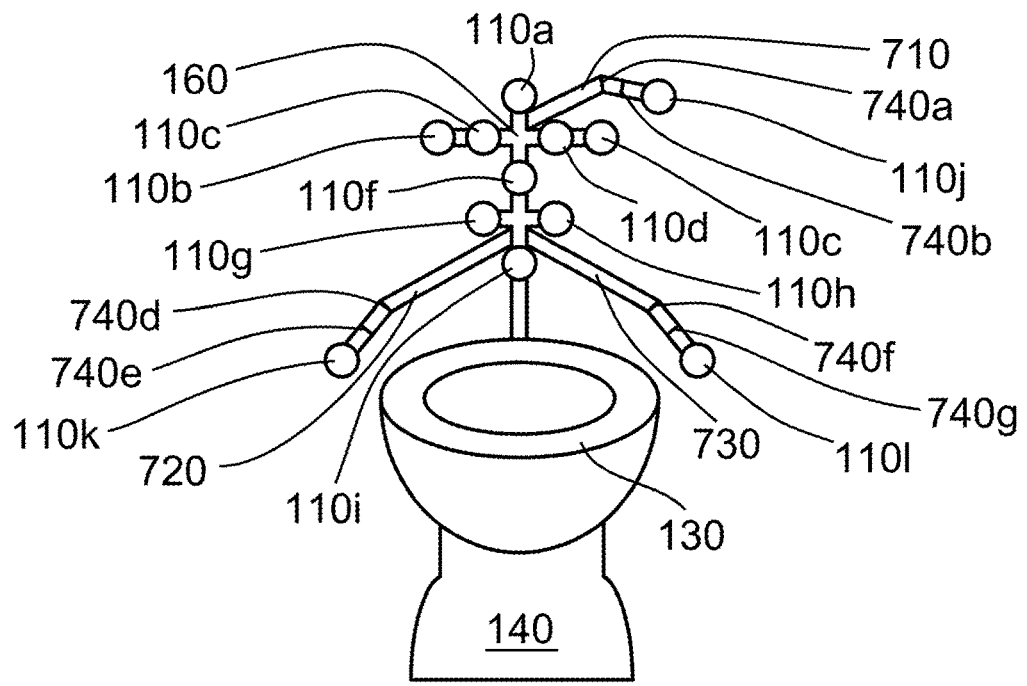
FIG. 7A illustrates an embodiment of the disclosed sensor platform array with sensors mounted on a support structure with hinged arms.
Figure 7B:
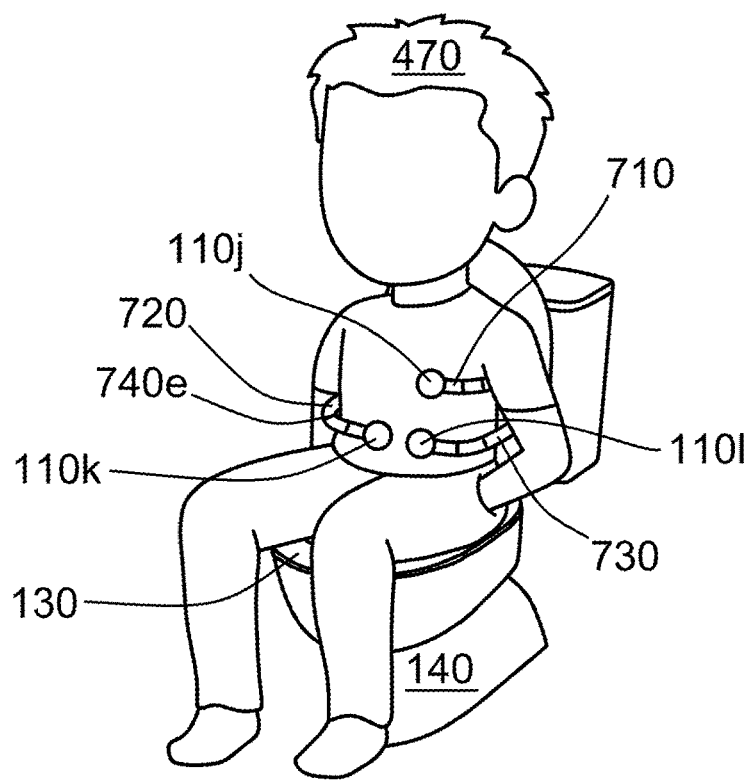
FIG. 7B illustrates the embodiment of FIG. 4A mounted on a medical toilet with a user seated thereon.

FIG. 7A illustrates an embodiment of the disclosed sensor platform array which includes sensor platforms 110a-i and support structure 160. These are substantially the same as shown in the embodiment of FIGS. 1A and 1B. Also included in the embodiment of FIG. 7A are arms 710, 720, and 730 which extend outward from support structure 160. Sensor platform 110j is positioned on the distal end of arm 710, furthest from support structure 160. Similarly, sensor platform 110k is positioned on the distal end of arm 720 and sensor platform 110l is positioned on the distal end of arm 730. Arm 710 includes hinges 740a and 740b, arm 720 includes hinges 740c and 740d, and arm 730 includes hinges 740e and 740f. Each of arms 710, 720, and 730 bend at their respective hinges enabling the arms to wrap around user 470 as shown in FIG. 7B. User 470 is shown seated on toilet seat 130 in FIG. 7B. Arms 710, 720, and 730 bend through hinges 740a-f and wrap around the torso of user 470. Sensor platforms 110j, 110k, and 110l are disposed on the chest and abdomen of user 470. Sensor platform 110j may support a sensor which collects measurements from a user's heart, for example, a stethoscope. Sensor platforms 110k and 110l may support sensors which collect measurements from a user's intestine or other abdominal organs. For example, sensor platform 110l may support an ultrasound probe which may collect images of the user's abdominal organs. Sensor platform 110l may support a stethoscope which may detect bowel sounds or a temperature sensor which may detect skin temperature.

In some embodiments, cell pressure sensors 110a-l may monitor body movement through detection in changes in pressure. Small movements may be detected which may be used to collect measurements which may be relevant to a user's health and well-being. For example, small body movements may arise from heart beat and blood flow (ballistocardiography), breathing, and peristaltic contraction of the intestine. Larger movements may also be detected and used to detect other events related to health and wellness, for example, coughing, muscle spasms, tremors, and other events involving musculoskeletal movement.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A sensor platform array comprising:
   a support panel;
   a plurality of sensor-inflatable cell assemblies, each assembly comprising:
      an inflatable cell; and
      a sensor, wherein the sensor is mounted on the inflatable cell, wherein each of the plurality of sensor-inflatable cell assemblies is connected to the support panel, and wherein the sensor collects physiological measurements;
   a gas pump, wherein in the gas pump is in fluid connection with the air inflatable cell in each of the plurality of sensor-inflatable cell assemblies and is configured to pump gas independently to each of the plurality of inflatable cells; and
   a toilet lid, wherein the support panel is mounted on the toilet lid.

2. The sensor platform array of claim 1, further comprising a conformation control system, the conformation control system comprising:
   a plurality of pressure sensors, wherein each of the plurality of pressure sensors is in communication with the inflatable cell within one of the plurality of sensor-inflatable cell assemblies;
   a controller, wherein the controller is in electronic communication with each of the plurality of pressure sensors; and
   a non-transitory computer readable medium comprising instructions for actuating the pump and directing the pump to provide a supply of gas to the inflatable cell in each of the plurality of assemblies in the absence of a signal from the pressure sensor.

3. The sensor platform array of claim 2, wherein the non-transitory computer readable medium further comprises instructions for independently halting the supply of gas to each of the at least one inflatable cell in response to a signal from the pressure sensor on the sensor platform.

4. The sensor platform array of claim 1, wherein the sensor is independently selected from the following list: a stethoscope, an ultrasound probe, an echocardiogram probe, a temperature sensor, a durometer, an electrocardiogram lead, and a ballistocardiography sensor.

5. The sensor platform array of claim 1, wherein the sensors are removable and exchangeable with other sensors.

6. The sensor platform array of claim 1, further comprising at least one bendable arm, wherein each of the at least one bendable arm comprises:
   at least one sensor; and
   at least one hinge;
   wherein the at least one bendable arm extends from the support panel.

7. The sensor platform array of claim 1, wherein the sensor within each of plurality of sensor-inflatable cell assemblies is in electrical communication with the controller.

8. The sensor platform array of claim 7 wherein the controller comprises a memory, and wherein the controller stores a signal produced by the sensor within each of the plurality of sensor-inflatable cell assemblies on the memory.

9. The sensor platform array of claim 8, further comprising a non-transitory computer readable medium comprising instructions for creating an analysis of the signal produced by the sensor within each of the plurality of sensor-inflatable cell assemblies.

10. A sensor platform array comprising:
    a support panel;
    an inflatable cell, wherein the inflatable cell is mounted on the support panel;
    a plurality of sensors, wherein each of the plurality of sensors is mounted on the inflatable cell; and
    a gas pump, wherein in the gas pump is in fluid connection with the inflatable cell; and
    a toilet lid, wherein the support panel is mounted on the toilet lid.

11. The sensor platform array of claim 10, further comprising a conformation control system comprising:
    a plurality of pressure sensors, wherein each of the plurality of pressure sensors is in communication with the inflatable cell;
    a controller; and
    a non-transitory computer readable medium comprising instructions for actuating the pump to pump gas into the inflatable cell.

12. The sensor platform array of claim 11, wherein the non-transitory computer readable medium further comprises instructions for deactivating pump in response to a signal from at least one of the plurality of pressure sensors.

13. The sensor platform array of claim 10, wherein each of the plurality of sensors is independently selected from the following list: a stethoscope, an ultrasound probe, an echocardiogram probe, a temperature sensor, a durometer, an electrocardiogram lead, and a ballistocardiography sensor.

14. The sensor platform array of claim 10, wherein each of the plurality of sensors is removable and exchangeable with other sensors.

15. The sensor platform array of claim 10, further comprising at least one bendable arm, wherein each of the at least one bendable arm comprises:
    at least one sensor; and
    at least one hinge;
    wherein the at least one bendable arm extends from the support panel.

16. The sensor platform array of claim 10, wherein each of the plurality of sensors is in electrical communication with the controller.

17. The sensor platform array of claim 16 wherein the controller comprises a memory, and wherein the controller stores a signal produced by each of the plurality of sensors on the memory.

18. The sensor platform array of claim 17, further comprising a non-transitory computer readable medium comprising instructions for creating an analysis of the signal produced by each of the plurality of sensors.

* * * * *